(12) United States Patent
Friesen et al.

(10) Patent No.: US 7,951,403 B2
(45) Date of Patent: May 31, 2011

(54) METHOD OF MAKING PHARMACEUTICAL MULTIPARTICULATES

(75) Inventors: Dwayne T. Friesen, Bend, OR (US); Marshall D. Crew, Bend, OR (US); Roderick J. Ray, Bend, OR (US); Leah E. Appel, Bend, OR (US)

(73) Assignee: Pfizer Inc., New York, NY (US)

( * ) Notice: Subject to any disclaimer, the term of this patent is extended or adjusted under 35 U.S.C. 154(b) by 1588 days.

(21) Appl. No.: 11/003,659

(22) Filed: Dec. 3, 2004

(65) Prior Publication Data

US 2005/0181060 A1    Aug. 18, 2005

Related U.S. Application Data

(60) Provisional application No. 60/527,316, filed on Dec. 4, 2003.

(51) Int. Cl.
*A61K 9/14* (2006.01)
*A61K 9/16* (2006.01)
(52) U.S. Cl. .................. 424/498; 424/489
(58) Field of Classification Search .......... None
See application file for complete search history.

(56) References Cited

U.S. PATENT DOCUMENTS

| | | | |
|---|---|---|---|
| 2,955,956 A | 10/1960 | Baugh et al. | 117/100 |
| 3,900,561 A * | 8/1975 | Davis et al. | 514/177 |
| 4,053,264 A | 10/1977 | King | 425/8 |
| 4,086,346 A | 4/1978 | Bocker et al. | 424/253 |
| 4,092,089 A | 5/1978 | Bocker et al. | 425/10 |
| 4,145,307 A * | 3/1979 | Krapf et al. | 516/27 |
| 4,230,566 A * | 10/1980 | Faudree, III | 210/693 |
| 4,293,570 A | 10/1981 | Vadasz | 426/3 |
| 4,474,768 A | 10/1984 | Bright | 424/180 |
| 4,517,359 A | 5/1985 | Kobrehel et al. | 536/7.4 |
| 4,675,140 A | 6/1987 | Sparks et al. | 264/4.3 |
| 4,874,611 A | 10/1989 | Wilson et al. | 424/410 |
| 4,931,285 A | 6/1990 | Edgren et al. | 424/473 |
| 4,957,681 A | 9/1990 | Klimesch et al. | 264/211.23 |
| 4,963,531 A | 10/1990 | Remington et al. | 514/29 |
| 5,019,302 A | 5/1991 | Sparks et al. | 264/8 |
| 5,024,842 A | 6/1991 | Edgren et al. | 424/473 |
| 5,047,244 A | 9/1991 | Sanvordeker et al. | 424/435 |
| 5,064,650 A | 11/1991 | Lew | 424/435 |
| 5,084,287 A | 1/1992 | Ghebre-Sellassie et al. | 424/495 |
| 5,100,592 A | 3/1992 | Sparks et al. | 264/7 |
| 5,143,662 A | 9/1992 | Chesterfield et al. | 264/8 |
| 5,160,743 A | 11/1992 | Edgren et al. | 424/473 |
| 5,169,645 A | 12/1992 | Shukla et al. | 424/499 |
| 5,183,690 A | 2/1993 | Carr et al. | 427/213.31 |
| 5,194,262 A | 3/1993 | Goldberg et al. | 424/401 |
| 5,196,199 A | 3/1993 | Fuisz | 424/401 |
| 5,213,810 A | 5/1993 | Steber | 424/490 |
| 5,219,572 A * | 6/1993 | Sivaramakrishnan et al. | 424/438 |
| 5,236,734 A | 8/1993 | Fuisz | 426/641 |
| 5,292,657 A | 3/1994 | Rutherford et al. | 435/243 |
| 5,348,758 A | 9/1994 | Fuisz et al. | 426/660 |
| 5,380,473 A | 1/1995 | Bogue et al. | 264/11 |
| 5,405,617 A | 4/1995 | Gowan, Jr. et al. | 424/464 |
| 5,407,676 A | 4/1995 | Fuisz | 424/401 |
| 5,429,836 A | 7/1995 | Fuisz | 426/601 |
| 5,433,951 A | 7/1995 | Serajuddin et al. | 424/486 |
| 5,456,932 A | 10/1995 | Fuisz et al. | 426/548 |
| 5,461,089 A | 10/1995 | Handyside et al. | 523/171 |
| 5,500,162 A | 3/1996 | Theisen et al. | 264/9 |
| 5,501,858 A | 3/1996 | Fuisz | 424/439 |
| 5,505,983 A | 4/1996 | Kamada | 427/2.21 |
| 5,518,730 A | 5/1996 | Fuisz | 424/426 |
| 5,539,000 A | 7/1996 | Leonard | 514/682 |
| 5,549,917 A | 8/1996 | Cherukuri et al. | 426/96 |
| 5,556,652 A | 9/1996 | Cherukari et al. | 426/5 |
| 5,569,467 A | 10/1996 | Ruiz | 424/489 |
| 5,582,855 A | 12/1996 | Cherukuri et al. | 426/5 |
| 5,597,416 A | 1/1997 | Fuisz et al. | 127/30 |
| 5,597,844 A | 1/1997 | Chauhan et al. | 514/400 |
| 5,601,761 A | 2/1997 | Hoffman et al. | 264/4.3 |
| 5,605,889 A | 2/1997 | Curatolo et al. | 514/29 |
| 5,633,006 A | 5/1997 | Catania et al. | 424/441 |
| 5,683,720 A | 11/1997 | Myers et al. | 424/489 |
| 5,690,959 A | 11/1997 | Palepu et al. | 424/472 |
| 5,705,190 A | 1/1998 | Broad et al. | 424/465 |
| 5,707,646 A | 1/1998 | Yajima et al. | 424/439 |
| 5,733,577 A | 3/1998 | Myers et al. | 424/488 |
| 5,741,519 A | 4/1998 | Rosenberg et al. | 424/464 |
| 5,744,180 A | 4/1998 | Cherukuri et al. | 426/99 |
| 5,747,058 A | 5/1998 | Tipton et al. | 424/423 |
| 5,766,521 A | 6/1998 | Le Thiesse et al. | 264/7 |
| 5,792,474 A | 8/1998 | Rauchfuss | 424/489 |
| 5,824,342 A | 10/1998 | Cherukuri et al. | 424/484 |
| 5,840,334 A | 11/1998 | Raiden et al. | 424/464 |
| 5,849,223 A | 12/1998 | Myers et al. | 264/15 |
| 5,851,553 A | 12/1998 | Myers et al. | 424/488 |
| 5,851,555 A | 12/1998 | Sanghvi et al. | 424/464 |
| 5,855,915 A | 1/1999 | Pinkus | 242/486 |
| 5,869,098 A | 2/1999 | Misra et al. | 424/484 |
| 5,869,101 A | 2/1999 | Moller et al. | 424/489 |
| 5,883,103 A | 3/1999 | Burnside et al. | 514/262 |
| 5,891,845 A | 4/1999 | Myers | 514/11 |
| 5,912,030 A | 6/1999 | Huzinec et al. | 426/3 |

(Continued)

FOREIGN PATENT DOCUMENTS

EP    0080341    6/1983

(Continued)

OTHER PUBLICATIONS

Khankari et al. Pharmaceutical hydrates. Thermochimica Acta 1995 248:61-79.*

(Continued)

*Primary Examiner* — Juliet C Switzer
*Assistant Examiner* — Caralynne Helm
(74) *Attorney, Agent, or Firm* — Jennifer Kispert; J. Michael Dixon

(57) ABSTRACT

A process for forming drug multiparticulates having improved drug crystallinity is disclosed, comprising modifying a conventional melt-congeal process by adding a volatile cospecies either to the molten mixture or to the process atmosphere, or to both.

6 Claims, No Drawings

U.S. PATENT DOCUMENTS

| | | | |
|---|---|---|---|
| 5,919,489 A | 7/1999 | Saleki-Gerhardt et al. | 424/501 |
| 5,935,600 A | 8/1999 | Cherukuri et al. | 424/464 |
| 5,948,407 A | 9/1999 | McGuinness et al. | 424/184.1 |
| 5,952,004 A | 9/1999 | Rudnic et al. | 424/455 |
| 5,958,452 A | 9/1999 | Oshlack et al. | 424/457 |
| 5,965,161 A | 10/1999 | Oshlack et al. | 424/457 |
| 5,965,164 A | 10/1999 | Fuisz et al. | 424/489 |
| 5,972,373 A | 10/1999 | Yajima et al. | 424/439 |
| 5,980,941 A | 11/1999 | Raiden et al. | 424/464 |
| 6,001,391 A * | 12/1999 | Zeidler et al. | 424/467 |
| 6,010,718 A | 1/2000 | Al-Razzak et al. | 424/464 |
| 6,013,280 A | 1/2000 | Frisbee et al. | 424/464 |
| 6,048,541 A | 4/2000 | Mirsa et al. | 424/401 |
| 6,051,253 A | 4/2000 | Zettler et al. | 424/465 |
| 6,068,859 A | 5/2000 | Curatolo et al. | 424/490 |
| 6,077,541 A | 6/2000 | Chen et al. | 424/480 |
| 6,083,430 A | 7/2000 | Fuisz et al. | 264/5 |
| 6,086,920 A | 7/2000 | Frisbee et al. | 424/489 |
| 6,090,830 A | 7/2000 | Myers et al. | 514/356 |
| 6,103,264 A | 8/2000 | Hoffmann et al. | 424/468 |
| 6,117,452 A | 9/2000 | Ahlgren et al. | 424/468 |
| 6,139,872 A | 10/2000 | Walsh | 424/464 |
| 6,165,512 A | 12/2000 | Mezaache et al. | 424/489 |
| 6,221,368 B1 | 4/2001 | Breitenbach et al. | 424/400 |
| 6,245,903 B1 | 6/2001 | Karimian et al. | 536/7.4 |
| 6,248,363 B1 | 6/2001 | Patel et al. | 424/497 |
| 6,261,599 B1 | 7/2001 | Oshlack et al. | 424/457 |
| 6,268,489 B1 | 7/2001 | Allen et al. | 536/7.4 |
| 6,270,799 B1 * | 8/2001 | Siefert et al. | 424/474 |
| 6,270,804 B1 | 8/2001 | Getz et al. | 424/490 |
| 6,287,693 B1 * | 9/2001 | Savoir et al. | 428/402 |
| 6,328,993 B1 | 12/2001 | Linder et al. | 424/451 |
| 6,335,033 B2 | 1/2002 | Oshlack et al. | 424/457 |
| 6,365,574 B2 | 4/2002 | Singer et al. | 514/29 |
| 6,383,510 B1 | 5/2002 | Linder et al. | 424/464 |
| 6,395,300 B1 | 5/2002 | Straub et al. | 424/489 |
| 6,423,345 B2 | 7/2002 | Bernstein et al. | 424/501 |
| 6,451,990 B1 * | 9/2002 | Bayod Jasanada et al. | 536/7.4 |
| 6,500,459 B1 | 12/2002 | Chhabra et al. | 424/474 |
| 6,551,616 B1 | 4/2003 | Notario et al. | 424/464 |
| 6,569,463 B2 | 5/2003 | Patel et al. | 424/497 |
| 6,576,258 B1 | 6/2003 | Kofler et al. | 424/458 |
| 6,645,528 B1 | 11/2003 | Straub et al. | 424/489 |
| 6,682,759 B2 | 1/2004 | Lim et al. | 424/468 |
| 6,689,390 B2 | 2/2004 | Bernstein et al. | 424/501 |
| 6,692,767 B2 | 2/2004 | Burnside et al. | 424/489 |
| 6,984,403 B2 | 1/2006 | Hagen et al. | |
| 2001/0003590 A1 | 6/2001 | Joachim et al. | 424/465 |
| 2001/0006650 A1 | 7/2001 | Burnside et al. | 424/400 |
| 2001/0048946 A1 * | 12/2001 | Ghebre-Sellassie | 424/486 |
| 2002/0009433 A1 | 1/2002 | Curatolo et al. | 424/94.1 |
| 2002/0025342 A1 | 2/2002 | Linder et al. | 424/489 |
| 2002/0044965 A1 * | 4/2002 | Curatolo et al. | 424/468 |
| 2002/0044968 A1 | 4/2002 | Van Lengerich | 424/469 |
| 2002/0111318 A1 * | 8/2002 | Rengaraju | 514/29 |
| 2003/0165563 A1 | 9/2003 | Murphy et al. | 424/465 |
| 2003/0190365 A1 | 10/2003 | Fergione et al. | 424/489 |
| 2003/0228357 A1 | 12/2003 | Johnson et al. | 424/465 |
| 2004/0014951 A1 | 1/2004 | Dumic et al. | 536/7.1 |
| 2004/0023898 A1 | 2/2004 | Dunne | |
| 2004/0121003 A1 | 6/2004 | Chickering, III et al. | 424/465 |
| 2005/0026851 A1 | 2/2005 | Danilovski et al. | 514/28 |
| 2005/0123615 A1 * | 6/2005 | Ray et al. | 424/489 |

FOREIGN PATENT DOCUMENTS

| | | |
|---|---|---|
| EP | 0109253 | 5/1984 |
| EP | 0582396 | 2/1994 |
| EP | 0925789 | 6/1999 |
| EP | 0943341 | 9/1999 |
| EP | 0776658 | 2/2000 |
| EP | 1127580 | 8/2001 |
| GB | 2066070 | 7/1981 |
| GB | 2091097 | 7/1982 |
| IN | 187487 | 5/2000 |
| WO | WO9107171 | 5/1991 |
| WO | WO-9311749 * | 6/1993 |
| WO | WO9400112 | 1/1994 |
| WO | WO9427557 | 12/1994 |
| WO | WO9509601 | 4/1995 |
| WO | WO9806714 | 2/1998 |
| WO | WO9818610 | 5/1998 |
| WO | 9841193 | 9/1998 |
| WO | WO9846239 | 10/1998 |
| WO | WO9856357 | 12/1998 |
| WO | WO9903453 | 1/1999 |
| WO | WO9924031 | 5/1999 |
| WO | WO0026285 | 5/2000 |
| WO | WO0057886 | 10/2000 |
| WO | WO0142221 | 6/2001 |
| WO | WO0178688 | 10/2001 |
| WO | WO0185135 | 11/2001 |
| WO | WO0224174 | 3/2002 |
| WO | WO02064121 | 8/2002 |
| WO | WO03018031 | 3/2003 |
| WO | WO03032922 | 4/2003 |
| WO | WO03037304 | 5/2003 |
| WO | WO03053402 | 7/2003 |
| WO | 03066655 | 8/2003 |
| WO | WO03063832 | 8/2003 |
| WO | WO03063833 | 8/2003 |
| WO | WO03063834 | 8/2003 |
| WO | WO03068191 | 8/2003 |
| WO | WO03105810 | 12/2003 |
| WO | WO04000865 | 12/2003 |
| WO | WO2004009608 | 1/2004 |
| WO | WO2004035063 | 4/2004 |
| WO | WO2004087096 | 10/2004 |

OTHER PUBLICATIONS

BASF Food Emulsifiers Guide.*
Mazol® PGO 104K Product Sheet.*
Gandhi et al. European Journal of Pharmaceutical Sciences 2002 16:175-184.*
BASF Food Emulsifiers Guide 1999 p. 1-4.*
Mazol® PGO 104K Product Sheet 2002 p. 1.*
Savolainen, Marja et al., International Journal of Pharmaceutics, Aug. 27, 2003, vol. 262, No. 1-2., pp. 47-62, "Evaluation of polar lipid-hydrophilic polymer microparticles."
Foulds, G., et al., "The effects of an antacid or cimetidine on the serum concentrations of azithromycin", J. Clin. Pharmacol. Feb. 1991; 31(2): 164-7 (Abstract).
Amsden, G.W., et al., "Serum and WBC pharmacokinetics of 1500 mg of azithromycin when given either as a single dose or over a 3 day period in healthy volunteers", J. Antimicrobial Chemotherapy (2001), 47(1), 61-66 (Abstract).
Zithromax® azithromycin tablet 250 mg, Quantitative Composition of the Tablet Blend.
Zithromax® azithromycin for oral suspension composition 200 mg/5mL, 200mg/5mL Drug Product.
Zithromax® azithromycin for oral suspension composition 1 gram sachet, Quantitative Composition of the Drug Product.
Zithromax® azithromycin for oral suspension composition 100 mg/5mL, Quantitative Compositions of the Drug Products.
Zithromax® (azithromycin tablets and azithromycin for oral suspension), Full U.S. Prescribing Information, 70-5179-00-4.
Zithromax® (azithromycin capsules) (azithromycin tablets) and (azithromycin for oral suspension), Full U.S. Prescribing Information, 69-4763-00-9.
Food and Drug Administration Center for Drug Evaluation and Research Approved Drug Products with Therapeutic Evaluations, 24th Edition, Orange Book Listings of Azithromycin Dosage Forms.
Barber, J., "Assignments of the $^{13}$C and $_1$H NMR Spectra of Azithromycin in $CDCl_3$," Magnetic Resonance in Chemistry 29:7(1991)740-743.
Barthelemy, P., et al., "Compritol® 888 ATO: An Innovative Hot-Melt Coating Agent for Prolonged-Release Drug Formulations," *Europ. J. Pharmaceut. and Biopharmaceutics*, 47(1999)87-90.
Bhagwatwar, H., et al., "Preparation of Drug-Containing Wax Microspheres Using a Melt Dispersion Technique," *Pharmaceutical Research*, 6:7(1989)S-177, Abstract No. PD 1201.

Breitenbach, J., et al., "Solid Dispersions by an Integrated Melt Extrusion System," *Proceed. Int'l Symp. Control. Re. Bioact. Materials*, 25(1998)804-805.

Craig, D.Q.M., "The Physical Characterisation of Gelucire 50/13," *Bulletin Technique Gattefosse*, 89(1996)39-51.

DeMan, J.M., et al., "Thermal Analysis Microscopy for the Study of Phase Changes in Fats," *Food Microstructure*, 4(1985)233-239.

Eldem T., et al., "Polymorphic Behavior of Sprayed Lipid Micropellets and Its Evaluation by Differential Scanning Calorimetry and Scanning Electron Microscopy," *Pharmaceutical Research*, 8:2(1991)178-184.

Eldem, T., et al., "Optimization of Spray-Dried and -Congealed Lipid Micropellets and Characterization of Their Surface Morphology by Scanning Electron Microscopy," *Pharmaceutical Research*, 8:1(1991)47-54.

Emas, M., and H. Nyqvist, "Methods of Studying Aging and Stabilization of Spray-Congealed Solid Dispersions with Carnauba Wax. 1. Microcalorimetric Investigation," *Int'l J. Pharmaceutics*, 197(2000)117-127.

Faham, A., et al., "Hot-Melt Coating Technology. I. Influence of Compritol 888 Ato and Granule Size on Theophylline Release," *Drug Dev. Industrial Pharm.*, 26:2(2000)167-176.

Follonier, N., et al, "Hot-Melt Extruded Pellets for the Sustained Release of Highly Dosed Freely Soluble Drugs," *Proceed. Intern. Symp. Control. Release Bioactive Materials*, 18(1991)578-579.

Forster, A., et al., "Characterization of Glass Solutions of Poorly Water-Soluble Drugs Produced by Melt Extrusion with Hydrophilic Amorphous Polymers," *J. Pharmacy Pharmacology*, 53(2001)303-315.

Foulds, G., et al., "The Absence of an Effect of Food on the Bioavailability of Azithromycin Administered as Tablets, Sachet or Suspension," *J. Antimicrobial Chemotherapy*, 37:Suppl. C(1996)37-44.

Gattefosse, "Gelucire® —Pharmaceutical Excipients for Oral Semi-Solid Formulations," Technical Dossier, $2^{nd}$ edition, Gattefosse s.a., Cedex, France (1996).

Ghali, E.S., et al., "Thermal Treatment of Beads with Wax for Controlled Release,". *Drug, Development and Industrial Pharmacy*, 15:9(1989)1311-1328.

Hancock, B.C., and G. Zografi, "The Relationship Between the Glass Transition Temperature and the Water Content of Amorphous Pharmaceutical Solids," *Pharmaceutical Research*, 11:4(1994)471-477.

Joachim, J., et al., "Le Compritol", Etudes Galenique, Physique et Statstique, *APGI*, IV(1989)291-296.

Johnson, D.E., et al., "A New Method for Coating Glass Beads for Use in Gas Chromatography of Chloropromazine and Its Metabolites," Source unknown, and date unknown. (May be 1964-1965).

Jorgensen, K., et al., "Dissolution Stability of Multiparticulate Controlled Release Tablets," *Int'l J. Pharmaceutics*, 153(1997)1-11.

Meshall, M.M., et al., "Optimization of Theophylline Release from Tablets Containing Compritol," *S.T.P. Pharma Sciences*, 5:6(1995)429-434.

Perez, M. deLos A, et al.. "Sustained Release Phenylpropanolamine Hydrochloride from Compritol ATO-888 Matrix," *Pharmaceutical Research*, 9:10(1992)S-162, Abstract No. PT6191.

Perez, M.A., et al., "Sustained Release Phenylpropanolamine Hydrochloride from ATO 888 Matrix " *PRHSJ*, 12:4(1993)263-267.

Perissutti, B., et al., "Solid Dispersions of Carbamazepine with Gelucire 44/14 and 50/13," *S.T.P. Pharma Sciences*, 10:6(2000)479-484.

Physician's Desk Reference, Information cited on ZITHROMAX® capsules (equivalent to 250 mg azithromycin), tablets (equivalent to 600 mg azithromycin), and oral suspension (equivalent to 1 g azithromycin).

Reilly, W.J. Jr., and J.B. Schwartz, "A Potential Controlled Release Wax Matrix Excipient," *Pharmaceutical Research*, 8:10(1991)98, supplement, Abstract No. PT6108.

Reis, R. and F. Moll, "Matrix Formation of Polyglycolic Acid Tablets by Annealing," *European J. Pharm. and Biopharm.*, 40:1(1994)14-18.

Rxlist.com, "Azithromycin," description of drug, categories, brand names, from internet website, Mar. 14, 2001.

San Vincente, A., et al., "Effect of Aging on the Release of Salbutamol Sulfate from Lipid Matrices," *Int'l J. Pharmaceutics*, 208(2000)13-21).

Schwartz, J.B., et al., "A Potential Controlled Release Wax Matrix Excipient for Tablets," *Pharmaceutical Research*, 9:10(1992)S-162, Abstract No. PT6189.

Schwartz, J.B., et al., Preliminary Evaluation of Controlled Release Agents for Tablets, *Pharmaceutical Research*, 9:10(1992)S-162, Abstract No. PT6190.

Sugao, H., et al, "Taste Masking of Bitter Drug Powder without Loss of Bioavailability by Heat Treatment of Wax-Coated Microparticles," *J. Pharmaceutical Sci.*, 87:1(1998)96-100.

Thomsen, L.J., et al., "Prolonged Release Matrix Pellets Prepared by Melt Pelletization. I. Process Variables," *Drug Development and Industrial Pharmacy*, 19:15(1993)187-1887.

Wang, A.E. and J.B. Schwartz, "Effect of Temperature on Drug Release from Wax Matrix Tablets After Thermal Treatment," *Pharmaceutical Research*, 11:10(1994)S-155, Abstract No. 6099.

Zhang, Y.-E., et al., Effect of Processing Methods and Heat Treatment on the Formation of Wax Matrix Tablets for Sustained Drug Release, *Pharm. Dev. Technol.*, 6:2(2001)131-144.

Arguendas, A., "Single Dose Therapy in Otitis Media, *Clinical Microbiology and Infection*," Abstract, S130, vol. 5, Supplemental 3, (1999).

Block, S., et al., "Single-Dose Azithromycin (30 mg/kg) in Acute Otitis Media," ICAAC, New Orleans, LA, Sep. 7-10, 2003, Abstract 174.

Curatolo, W., et al., "Site-Specific Absorption and Toleration of Azithromycin," Proceedings Intern. Symposium Rel. Bioact. Mater., 23, 1996.

Luke, D.R., et al, "Clinical Pharmacology of Azithromycin Given at Various Sites Along the Gastrointestinal Tract in Healthy Subjects," pp. 464-468.

Physicians Desk Reference, "*Appendix A Summary of Pediatric Suspension Commercial Products*," $55^{th}$ edition, Phase III Clinical Dosage Form Nomination, pp. 19 and 28 (2001).

Pfizer, Inc., Zithromax [package insert], "*Zithromax (azithromycin tablets) and (azithromycin for oral suspension)*," www.pfizer.com/download/uspi_zithromax.pdf (2004).

Passerini, N., et al., Journal of Controlled Release, "Controlled release of verapamil hydrochloride from waxy microparticle prepared by spray congealing," vol. 88, No. 2, pp. 263-275, (2003).

Yajima, T., et al., Chemical and Pharmaceutical Bulletin, "Optimum heat treatment conditions for masking the bitterness of the clarithromycin wax matrix," vol. 51, No. 11, pp. 1223-1226, (2003).

International Preliminary Report on Patentability, Application No. PCT/IB2004/003903.

* cited by examiner

METHOD OF MAKING PHARMACEUTICAL MULTIPARTICULATES

The present application claims the priority benefit of U.S. Provisional Application No. 60/527,316, filed on Dec. 4, 2003. The contents of the priority document are herein incorporated by reference.

BACKGROUND OF THE INVENTION

The present invention relates to a method for making multiparticulates comprising crystalline drug suspended in a carrier that maintains the desired crystalline form of the drug in the multiparticulate.

It is well known that some drugs are capable of existing in several different crystalline forms. A specific example of a drug that may exist in one of several crystalline forms is azithromycin, for which at least 13 different crystalline forms have been identified thus far. See commonly owned U.S. Patent Application Publication No. 20030162730.

It is also well known that different crystalline forms of a drug may have different properties. For example, the different crystalline forms may vary as to water solubility, physical stability (the degree to which the form remains in its crystalline or amorphous state), chemical reactivity, and therapeutic efficacy.

Crystalline drugs may be administered in the form of multiparticulates. Multiparticulates comprise a multiplicity of particles whose totality represents the intended therapeutically useful dose of a drug. Other examples of multiparticulates are disclosed in, for example, *Multiparticulate Oral Drug Delivery* (Marcel Dekker, 1994), and *Pharmaceutical Pelletization Technology* (Marcel Dekker, 1989).

An especially effective method of forming multiparticulates is by a melt-congeal process. This process involves forming a molten mixture comprising the drug in the crystalline form and a carrier, atomizing the mixture to form droplets, and cooling the droplets to form the multiparticulates. One problem that arises when forming multiparticulates using a melt-congeal process is that the initial crystalline form of the drug is susceptible to changing from the desired crystalline form to another, less desirable form.

The conversion of a drug from one crystalline form to another during the process used to form the multiparticulate may be undesirable for any one of several reasons. The drug in one crystalline form may have properties that are superior to those of another crystalline form, such as a higher water solubility in one form compared with another. Alternatively, the drug when converted to the amorphous form or another crystalline form may have poorer chemical stability; for example the amorphous form or other crystalline form may be more reactive with the carrier or more prone to oxidation than the desired crystalline form. In addition, some crystalline forms may have different bioavailabilities.

What is therefore needed is a method for forming drug-containing multiparticulates wherein the conversion of the drug to another crystalline form or to the amorphous form is kept to acceptably low levels.

BRIEF SUMMARY OF THE INVENTION

Some crystalline drug forms include volatile species in the crystal structure. Examples of such crystalline forms and their corresponding volatile species include hydrates, which incorporate water; solvates, which incorporate a solvent; and a salt form, which incorporates a counterion which is capable of converting to a volatile species, such as an acetate or a hydrochloride. Azithromycin in the crystalline dihydrate form is an example of a crystalline form that includes the volatile species water. An example of a salt form of a crystalline drug that incorporates a counterion capable of converting to a volatile species is cetirizine hydrochloride, which includes a chloride counterion as a volatile species. One mechanism that causes some drugs to change forms during a melt-congeal process is that the crystalline form of the drug loses such a volatile species and converts from the initial or desired crystalline form to another crystalline form or to the amorphous form.

The present invention is an improved melt-congeal process for forming multiparticulates containing a drug in crystalline form wherein the crystalline form of the drug includes a volatile species, namely, the addition of the volatile species either to the molten mixture of drug and carrier or to an atmosphere in contact with the molten mixture (i) during the molten mixture's formation or (ii) during its formation into droplets or (iii) during both (i) and (ii). Preferably, sufficient volatile species is added that the activity of the volatile species in the molten mixture and/or in the atmosphere is equal to or greater than the activity of the volatile species in the crystalline form of the drug at the maximum operating temperature of the melt-congeal process. The unwanted conversion of crystalline drug forms to other forms is kept to acceptable levels by adding the volatile species, which effectively maintains a high activity of the volatile species in the molten mixture or in an atmosphere in contact with the molten mixture, or in both, thereby maintaining a low driving force for loss of the volatile species from the desired crystalline form, which in turn maintains the drug in the desired crystalline form during the formation of the multiparticulates, thereby forming multiparticulates wherein the drug is present substantially in its crystalline form.

In a separate embodiment, the multiparticulates are formed using a melt-congeal process comprising the steps: (a) providing a drug capable of existing in a crystalline form that includes a volatile species having a vapor pressure of at least 0.01 atmosphere at an operating temperature T; (b) forming a molten mixture comprising the drug and a carrier at the same temperature T; (c) forming droplets from the molten mixture; (d) solidifying the droplets in a congealing medium to form multiparticulates comprising the drug and the carrier; and (e) adding an amount of the volatile species in at least one of steps (b), (c) and (d). The drug may be initially present as (1) a crystalline drug form, (2) a mixture of crystalline drug forms, (3) amorphous drug, or (4) any combination of (1), (2) or (3). The amount of volatile species added in step (e) is sufficient to provide a relative degree of improvement in drug crystallinity of at least 1.1 in comparison to a multiparticulate made using a control method. The control method is the same as above, but without the addition of volatile species.

DETAILED DESCRIPTION OF PREFERRED EMBODIMENTS

The multiparticulates made by the process of the present invention comprise a crystalline drug and a carrier.

The term "multiparticulate" means a dosage form comprising a multiplicity of particles whose totality represents the intended therapeutically useful dose of the drug. The particles generally have a mean diameter from about 40 to about 3,000 μm, preferably from about 50 to about 1,000 μm and most preferably from about 100 to about 300 μm. While the multiparticulates can have any shape and texture, it is preferred that they be spherical, with a smooth surface texture. These physical characteristics tend to improve flow properties, "mouth feel," ease of swallowing and ease of uniform coating, if required.

As used in the present invention, the term "about" means the specified value ±10% of the specified value.

Drugs

The multiparticulates made by the process of the present invention include a drug. The term "drug" as used herein includes, by way of example and not of limitation, any physiologically or pharmacologically active substance that produces a localized or systemic effect in animals. The term "animals" is meant to include mammals, including human beings and other animals.

At least 70 wt % of the drug present in the multiparticulate formed by the inventive process should be in the desired crystalline form. Preferably, the drug in the composition is "substantially crystalline," meaning that the amount of drug in the desired crystalline form in the multiparticulate is at least about 80 wt %. More preferably, the drug in the composition is "almost completely crystalline," meaning that the amount of drug in the desired crystalline form in the multiparticulate is at least about 90 wt %. Most preferably, the drug in the multiparticulate is "essentially crystalline," meaning that the amount of drug in the desired crystalline form in the multiparticulate is at least about 95 wt %.

The drug may be any drug which may be administered in a crystalline form in multiparticulates, and in which the desired crystalline form includes a volatile species. The volatile species may be water or a solvent, or may be a counterion that is capable of conversion to a volatile form. In general, the volatile species should be sufficiently volatile that if the crystalline drug form is held in an open container at the maximum processing temperature of the melt-congeal process, a substantial portion of the volatile species is lost over a period of about 30 minutes. Generally, this means that the vapor pressure of the free form of the volatile species is at least 0.01 atm at the maximum operating temperature of the melt-congeal process. Preferably, the vapor pressure of the free form of the volatile species is at least 0.05 atm and more preferably at least 0.1 atm.

Exemplary crystalline forms incorporating water as the volatile species are drug hydrates, such as monohydrates, dihydrates, hemihydrates, sesquihydrates, etc. Exemplary drugs capable of existing in crystalline forms containing water include azithromycin dihydrate, sildenafil dihydrate, doxycycline monohydrate, ziprazidone hydrochloride monohydrate, penicillin G benzathine tetrahydrate, amoxicillin trihydrate and atorvastatin calcium trihydrate.

Other exemplary volatile species are solvents present in solvated crystal structures. Such solvents include ethanol, n-propanol, isopropanol, propylene glycol, cyclohexane, tetrahydrofuran, acetone and acetonitrile. The crystalline form may also include two or more volatile solvents, or one or more volatile solvents and water. Exemplary drugs capable of existing in crystalline solvate forms include azithromycin monohydrate/monocyclohexane solvate, azithromycin monohydrate/hemi-ethanol solvate, azithromycin monohydrate/monotetrahydrofuran solvate, azithromycin monohydrate/hemi-n-propanol solvate, and doxycycline HCl hemi-ethanolate hemihydrate.

Another exemplary volatile species is the chloride counterion, which may form hydrochloride salts with basic drugs. Under some processing conditions, the hydrochloride salt is removed from the drug crystal, liberating HCl and changing the crystal structure of the drug. Exemplary drugs capable of existing in crystalline forms including the chloride ion include cetirizine HCl, ziprasidone HCl, pseudoephedrine HCl, sertraline HCl, prazosin HCl, donepezil HCl, doxycycline HCl hemi-ethanolate hemihydrate, and doxepin HCl.

Yet another exemplary volatile species is the acetate counterion, which may form acetate salts with basic drugs. Under some processing conditions, the acetate salt is removed from the drug crystal, liberating acetic acid and changing the crystal structure of the drug. Exemplary drugs capable of existing in crystalline forms including the acetate ion include megestrol acetate, fludrocortisone acetate, mafenide acetate, norethindrone acetate, and cortisone acetate.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents, glycogen phosphorylase inhibitors, and cholesterol ester transfer protein inhibitors.

A preferred drug for use with the present invention is azithromycin. Azithromycin is the generic name for the drug 9a-aza-9a-methyl-9-deoxo-9a-homoerythromycin A, a broad-spectrum antimicrobial compound derived from erythromycin A. Accordingly, azithromycin and certain derivatives thereof are useful as antibiotics. Azithromycin can exist in a variety of crystalline forms, including a wide range of hydrates, solvates, and salt forms. The invention is suitable for all such forms where the crystalline form includes a volatile species as defined above. The various polymorphs of crystalline azithromycin are disclosed in U.S. Patent Application Publication No. 20030162730, published Aug. 28, 2003; U.S. Pat. Nos. 6,365,574 and 6,245,903; U.S. Patent Application Publication Nos. 20010047089, published Nov. 29, 2001, and 20020111318, published Aug. 15, 2002; and International Application Publication Nos. WO 01/00640, WO 01/49697, WO 02/10181 and WO 02/42315. In a preferred embodiment, the azithromycin is in the form of the crystalline dihydrate, described in U.S. Pat. No. 6,268,489.

Melt-Congeal Process

The multiparticulates are formed using a melt-congeal process, comprising three basic steps: (1) forming a molten mixture comprising the crystalline drug and carrier; (2) atomizing the molten mixture to form droplets; and (3) solidifying the droplets to form the multiparticulates. The inventors have found that one key to maintaining the desired crystalline form of the drug during a melt-congeal process is to maintain a high activity of volatile species in the molten mixture or in an atmosphere and/or fluid with which the molten mixture comes in contact or in both the mixture and the mixture's atmosphere. The activity of the volatile species in the molten mixture and/or atmosphere is preferably maintained so that it is equivalent to or greater than that in the desired crystalline form of the drug. This ensures that the volatile species present in the crystalline form of the drug remains at equilibrium with the molten mixture and/or atmosphere, thereby preventing loss of volatile species from the desired crystalline form of the drug to the molten mixture and/or to the atmosphere.

As used herein, the "activity" of the volatile species in crystalline drug is a relative measure of the free energy of the volatile species in a particular state, and is equal to the ratio of the fugacity of the volatile species in equilibrium with the volatile species in crystalline drug divided by the fugacity of the pure volatile species at the processing conditions. In simplified terms, activity is the concentration of volatile species normalized to (i) the concentration of pure liquid or pure solid volatile species, or (ii) the vapor pressure of volatile species in equilibrium with the pure solid or pure liquid volatile species, depending on the temperature. In many cases, the volatile species' activity may be approximated by the ratio of the partial pressure of volatile species in equilibrium with the volatile species in the crystalline drug divided by the saturation vapor pressure of the volatile species at the processing conditions. See, for example, Lewis et al., *Thermodynamics* (1961).

The activity of volatile species in crystalline drug at the processing conditions can be determined experimentally by, for example, a dynamic vapor sorption test as follows. A sample of the crystalline drug containing the volatile species is placed in a chamber containing an atmosphere saturated with the volatile species at the temperature and absolute pressure used during processing of the molten mixture. The sample is allowed to equilibrate at these conditions and the weight of the sample is then recorded. While maintaining the temperature and absolute pressure in the atmosphere, the weight of the sample of crystalline drug is monitored as the partial pressure of the volatile species in the atmosphere in the chamber is decreased. When the partial pressure of volatile species in the chamber decreases to below the level equivalent to the activity of volatile species in the crystalline drug, the sample will begin to lose weight as volatile species is lost from the crystal structure. From these data, the activity of volatile species in the crystalline drug at the processing conditions can be determined. One skilled in the art will realize that care should be taken during such an evaluation to ensure that any volatile species not part of the crystalline drug structure (e.g., volatile species absorbed or condensed onto the surface drug crystals) is accounted for.

Another way to determine the activity of volatile species in crystalline drug at the processing conditions is by measuring the change in the crystalline state of the drug as a function of the amount of volatile species present in the molten mixture. A series of blends of the crystalline drug, the carrier, and varying amounts of volatile species are prepared and placed into sealed containers. The containers are then heated to the processing temperature used to form the multiparticulates and held at this temperature for a period of time, such as 90 minutes. During this time, a sample of the container's atmosphere, i.e., the container's "headspace," can be taken and the partial pressure of volatile species in the headspace can be measured using standard techniques, such as by gas chromatography. The containers are then cooled and the concentration of the desired crystalline form of the drug in each sample can be determined using standard techniques, as described below. The concentration of the desired crystalline form of the drug in the sample is then plotted versus the amount of volatile species included in the blend or the concentration of volatile species present in the headspace. From these data, the activity of volatile species in the crystalline drug at the processing conditions can be determined.

The amount of the desired crystalline form of the drug in the samples and in multiparticulates can be determined using Powder X-Ray Diffraction (PXRD) analysis. In an exemplary procedure, PXRD analysis may be performed on a Bruker AXS D8 Advance diffractometer. In this analysis, samples of about 500 mg are packed in Lucite sample cups and the sample surface smoothed using a glass microscope slide to provide a consistently smooth sample surface that is level with the top of the sample cup. Samples are spun in the $\phi$ plane at a rate of 30 rpm to minimize crystal orientation effects. The X-ray source (S/B KCu$_\alpha$, $\lambda$=1.54 Å) is operated at a voltage of 45 kV and a current of 40 mA. Data for each sample are collected over a period of about 20 to 60 minutes in continuous detector scan mode at a scan speed of about 1 to 15 seconds/step and a step size of 0.02°/step. Diffractograms are collected over the 2θ range of 4° to 30°.

The crystallinity of the test sample is determined by comparison with two or more calibration standards consisting of physical mixtures of crystalline drug and carrier. Each physical mixture is blended together 15 minutes on a Turbula mixer. Using the instrument software, the area under the diffractogram curve is integrated over the 2θ range using a linear baseline. This integration range includes as many drug-specific peaks as possible while excluding carrier-related peaks. A linear calibration curve of percent crystalline drug versus the area under the diffractogram curve is generated from the calibration standards. The crystallinity of the test sample is then determined using these calibration results and the area under the curve for the test sample. Results are reported as a mean percent drug crystallinity by crystal mass.

As mentioned above, the activity of the volatile species in the molten mixture and/or in the atmosphere in contact with the molten mixture is preferably equivalent to or greater than that in the crystalline form of the drug while forming the multiparticulates. The preferred amount of volatile species to add to keep any loss of volatile species from the crystalline drug to acceptable levels can be determined from the tests described above. Preferably, the partial pressure of volatile species in any atmosphere in contact with the molten mixture should be equal to or greater than the partial pressure at which the crystalline drug sample begins to lose weight or changes crystalline form.

However, to reduce the rate of conversion of the desired crystalline form to an undesired form, it is only required to raise the activity of the volatile species in the molten mixture or atmosphere in contact with the molten mixture, either during its formation or during its formation into droplets to form the multiparticulates. The amount of volatile species added to either the molten mixture or to the atmosphere of concern may be less than the amount needed for the activity in the molten mixture or atmosphere of concern to equal the activity in the crystalline form. Even though the activity of the volatile species in the molten mixture or atmosphere of concern may not equal that in the crystalline form of the drug, the activity may be raised enough to reduce the loss of the desired crystalline form to an acceptable level.

It is desirable to add the volatile species in an amount sufficient that the amount of drug in the desired crystalline form in the multiparticulate is increased relative to a multiparticulate formed using a control process in which the volatile species is not added. The control process is the same process used to form the multiparticulate but without the addition of the volatile species apart from the crystalline form itself. For example, in a process used to form a multiparticulate comprising a hydrate in which water is added during the process, no water would be added during the control process.

One useful measure for evaluating the amount of volatile species to add during the melt-congeal process is to determine a relative degree of improvement in crystallinity, meaning the ratio of (1) the amount of drug in a multiparticulate formed using a control process which is not in the desired crystalline form to (2) the amount of drug in a multiparticulate formed by a process of the invention which is not in the desired crystalline form. The amount of drug not in the desired crystalline form may be taken as 100 wt % minus the amount of drug in the desired crystalline form. For example, if the amount of drug in the multiparticulate formed by the control process which is in the desired crystalline form is 75 wt %, and the amount of drug in the multiparticulate formed by the process of the invention which is in the desired crystalline form is 80 wt %, the relative degree of improvement in crystallinity is (100 wt %–75 wt %)/(100 wt %–80 wt %) or 1.25.

An additional amount of volatile species is added to the molten mixture or to a process atmosphere during the melt-congeal process in an amount sufficient to cause a relative degree of improvement in crystallinity of greater than 1, preferably at least 1.1, more preferably at least 1.25, more preferably at least 1.5, even more preferably at least 2, and most preferably at least 3.

In general, the amount of volatile species added depends on the nature of the crystalline form of the drug, the excipients in the molten mixture, and the processing conditions. Where the volatile species is added to one of the processing atmospheres, the volatile species may be added in an amount of 30%, 50% or up to 100% or more of the saturation vapor pressure in the atmosphere of concern at the process conditions. Where the volatile species is added to the molten mixture, the volatile species may be added in an amount of 30%, 50%, or up to 100% or more of the solubility of the volatile species in the molten mixture at the process conditions. For some crystalline forms, a smaller amount of volatile species may be added to achieve acceptable levels of drug in the desired crystalline form in the resulting multiparticulate.

The amount of volatile species present in the molten mixture and/or in a processing atmosphere should be high enough so that at least 70 wt %, more preferably at least 80 wt %, and even more preferably at least 90 wt % of the drug in the multiparticulates is in the desired crystalline form.

The first step in the melt-congeal process is to combine the drug and carrier to form a molten mixture. As used herein, "molten mixture" refers to a suspension of substantially crystalline drug particles in a carrier heated sufficiently that the mixture becomes sufficiently fluid that the mixture may be formed into droplets or atomized. Atomization of the molten mixture may be carried out using any of the atomization methods described below. Generally, the mixture is molten in the sense that it will flow when subjected to one or more forces such as pressure, shear or centrifugal force, such as that exerted by a centrifugal or spinning-disk atomizer.

Generally, a mixture is sufficiently fluid for atomization when the viscosity of the molten mixture is less than about 20,000 cp, preferably less than about 15,000 cp, and most preferably less than about 10,000 cp. Often, the mixture becomes molten when the mixture is heated above the melting point of one or more of the carrier components, in cases where the carrier is sufficiently crystalline to have a relatively sharp melting point; or, when the carrier components are amorphous, above the softening point of one or more of the carrier components. In such cases, a portion of the drug may be dissolved in the fluid carrier and a portion of the carrier may remain solid.

Virtually any process may be used to form the molten mixture. One method involves heating the carrier in a tank until it is fluid and then adding the drug to the molten carrier. Generally, the carrier is heated to a temperature of about 10° C. or more above the temperature at which it becomes fluid. When one or more of the carrier components is crystalline, this is generally about 10° C. or more above the melting point of the lowest melting point material of the carrier. When the carrier comprises a mixture of carriers or when optional excipients are combined with the carrier, the carrier is heated to a temperature of about 10° C. or more above the melting point of the lowest melting point excipient or carrier in the composition. The process is carried out so that at least a portion of the feed remains fluid until atomized.

Once the carrier has become fluid, the drug may be added to the fluid carrier or "melt." Although the term "melt" generally refers specifically to the transition of a crystalline material from its crystalline to its liquid state, which occurs at its melting point, and the term "molten" generally refers to such a crystalline material in its fluid state, as used herein, the terms are used more broadly. In the case of "melt" the term refers to the heating of any material or mixture of materials sufficiently that it becomes fluid in the sense that it may be pumped or atomized in a manner similar to a crystalline material in the fluid state. Similarly, the term "molten" refers to any material or mixture of materials that is in such a fluid state. Alternatively, both the drug and the solid carrier may be added to the tank and the mixture heated until the carrier has become fluid.

Once the carrier has melted and the drug has been added, the feed mixture is mixed to ensure the drug is uniformly distributed in the molten mixture. Mixing is generally done using mechanical means, such as overhead mixers, magnetically driven mixers and stir bars, planetary mixers, and homogenizers. Optionally, the contents of the tank can be pumped out of the tank and through an in-line, static mixer or extruder and then returned to the tank. The amount of shear used to mix the molten mixture should be sufficiently high to ensure uniform distribution of the drug in the molten carrier. Since it is desired to keep the drug in the crystalline state, it is preferred that the shear not be so high such that the form of the drug is changed, i.e., so as to cause an increase in the amount of amorphous drug or a change in the crystalline form of the drug. It is also preferred that the shear not be so high as to reduce the particle size of the drug crystals. The molten mixture can be mixed from a few minutes to several hours, the mixing time being dependent on the viscosity of the molten mixture and the solubility of drug and any optional excipients in the carrier.

When preparing the molten mixture using such a tank system, the drug can be maintained in its initial crystalline form by ensuring that the activity of volatile species in the molten mixture is sufficiently high such that the volatile species in the drug crystals are not removed by dissolution into the molten mixture. This can be accomplished by adding an additional quantity of volatile species to the molten mixture, to the crystalline drug, or both, resulting in a high activity of volatile species in the molten mixture. For example, if the crystalline form of the drug is a hydrate, the crystalline hydrate may be converted to another crystalline form if it is contacted with dry molten carrier. One method to ensure that crystalline hydrate is not converted to another crystalline form by virtue of loss of water of hydration is to add a small amount of water to the molten feed to ensure there is sufficient water to prevent loss of the crystalline hydrate form.

In one embodiment, the molten mixture is in contact with a first atmosphere. The first atmosphere can be air, nitrogen, helium, argon, carbon dioxide, and the like. In such cases, an additional amount of the volatile species may be added to this first atmosphere to result in a sufficiently high activity of volatile species in the first atmosphere that the volatile species in the drug crystals are not removed by vaporization into the first atmosphere. Adding the additional amount of volatile species to the first atmosphere also helps maintain a high activity of volatile species in the molten mixture, also limiting loss of volatile species from the drug crystals.

Alternatively, where the volatile species is a solvent other than water, additional solvent is added to the atmosphere of concern and/or to the molten mixture. Where the volatile species is a counterion, the gas phase form of the volatile species may be added to a processing atmosphere. For example, where the counterion is the chloride ion, the atmosphere of concern may contain HCl. Alternatively, the ionic form of the counterion may be added in solution form. For example, an aqueous solution of HCl may be added to the molten mixture.

As a specific example of unwanted conversion of a stable crystalline form of drug to a less stable form, the inventors have found that when the most stable crystalline azithromycin dihydrate is contacted with dry molten carrier and a first atmosphere during formation of the molten mixture for a melt-congeal process, it is often converted into other less stable crystalline forms of azithromycin, such as the monohydrate. One method to ensure that crystalline azithromycin dihydrate is not converted to another less stable crystalline form by virtue of loss of water of hydration is to humidify the first atmosphere, e.g., by humidifying the headspace in the mixing tank during the mixing. Alternatively, a small amount of water, on the order of 30 to 100 wt % of the solubility of water in the molten mixture at the process temperature, can be added to the mixture to ensure the presence of sufficient water to minimize loss of the azithromycin dihydrate crystalline form. Alternatively, water may be added to both the tank headspace and to the molten mixture.

An alternative method of preparing the molten mixture is to use two tanks, melting a first excipient in one tank and a second in another. The drug is added to one of these tanks and mixed as described above. The same precautions regarding the activity of the volatile species in the tanks should be taken with such a dual tank system. The two melts are then pumped through an in-line static mixer or extruder to produce a single molten mixture that is directed to the atomization process described below. Such a dual system has advantages when one of the excipients reacts with the drug or when the excipients are mutually reactive, such as when one is a crosslinking agent that reacts with the second to form a crosslinked multiparticulate. An example of the latter is the use of an ionic crosslinking agent with alginic acid as the excipient.

Another method that can be used to prepare the molten mixture is to use a continuously stirred tank system. In this system, the drug and carrier are continuously added to a heated tank equipped with means for continuous stirring, while the molten mixture is continuously removed from the tank. The contents of the tank are heated so that the temperature of the contents is about 10° C. or more above the temperature at which the mixture becomes fluid. The drug and carrier are added in such proportions that the molten mixture removed from the tank has the desired composition. The drug is typically added in solid form and may be preheated prior to addition to the tank. The drug should be heated under conditions with sufficiently high volatile species activity to prevent loss of the volatile species from the crystalline form and consequent conversion of the crystalline form to another crystalline form or to the amorphous form. The carrier may also be preheated or even melted prior to addition to the continuously stirred tank system. A wide variety of mixing methods can be used with such a system, such as those described above, with care always being taken to maintain a high activity of the volatile species in the carrier and in the tank's first atmosphere in contact with the molten mixture so as to maintain the crystalline form of the drug.

An especially preferred method of forming the molten mixture is by an extruder. By "extruder" is meant a device or collection of devices that creates a molten extrudate by heat and/or shear forces and/or produces a uniformly mixed extrudate from a solid and/or liquid (e.g., molten) feed. Such devices include, but are not limited to single-screw extruders; twin-screw extruders, including co-rotating, counter-rotating, intermeshing, and non-intermeshing extruders; multiple screw extruders; ram extruders, consisting of a heated cylinder and a piston for extruding the molten feed; gear-pump extruders, consisting of a heated gear pump, generally counter-rotating, that simultaneously heats and pumps the molten feed; and conveyer extruders. Conveyer extruders comprise a conveyer means for transporting solid and/or powdered feeds, such, such as a screw conveyer or pneumatic conveyer, and a pump. At least a portion of the conveyer means is heated to a sufficiently high temperature to produce the molten mixture. The molten mixture may optionally be directed to an accumulation tank, before being directed to a pump, which directs the molten mixture to an atomizer. Optionally, an in-line mixer may be used before or after the pump to ensure the molten mixture is substantially homogeneous. In each of these extruders the molten mixture is mixed to form a uniformly mixed extrudate. Such mixing may be accomplished by various mechanical and processing means, including mixing elements, kneading elements, and shear mixing by backflow. Thus, in such devices, the composition is fed to the extruder, which produces a molten mixture that can be directed to the atomizer.

In one embodiment, the composition is fed to the extruder in the form of a solid powder, solid particles, or solid granules. The solid feed can be prepared using methods well known in the art for obtaining powdered mixtures with high content uniformity. See *Remington's Pharmaceutical Sciences* (16th Ed. 1980). Generally, it is desirable that the particle sizes of the drug and carrier be similar to obtain a uniform blend, although this is not essential to the successful practice of the invention.

An example of a process for preparing the blend is as follows. If necessary, the carrier is first milled so that its particle size is about the same as that of the drug; next, the drug and carrier are blended in a V-blender for 20 minutes; the resulting blend is then de-lumped to remove large particles and is finally blended for an additional 4 minutes. In some cases it is difficult to mill the carrier to the desired particle size since many of these materials tend to be waxy substances and the heat generated during the milling process can gum up the milling equipment. In such cases, small particles of the carrier can be formed using a melt- or spray-congeal process, as described below. The resulting congealed particles of carrier can then be blended with the drug to produce the feed for the extruder.

Another method for producing the feed to the extruder is to melt the carrier in a tank, mix in the drug as described above for a tank system, and then cool the molten mixture, producing a solidified mixture of drug and carrier. This solidified mixture can then be milled to a uniform particle size and fed to the extruder.

A two-feed extruder system can also be used to produce the molten mixture. In this system the carrier and crystalline drug, typically both in powdered form, are fed to the extruder through the same or different feed ports. In this way, the need for blending the components is eliminated.

Alternatively, the carrier in solid form may be fed to the extruder through a first delivery port, allowing the extruder to melt the carrier. The drug is then added to the molten carrier through a second feed delivery port located part way along the length of the extruder, thus reducing the contact time of the drug with the molten carrier. The closer the second feed delivery port is to the extruder exit, the lower is the residence time of drug in the extruder. Multiple-feed extruders can be used when the carrier comprises more than one excipient.

In another exemplary method, the composition is in the form of larger solid particles or a solid mass, rather than a powder, when fed to the extruder. For example, a solidified mixture can be prepared as described above and then molded to fit into the cylinder of a ram extruder and used directly without milling.

In another method, the carrier can be first melted in, for example, a tank, and fed to the extruder in molten form. The crystalline drug, typically in powdered form, may then be introduced to the extruder through the same or a different delivery port used to feed the carrier into the extruder. This system has the advantage of separating the melting step for the carrier from the mixing step, reducing the time of contact of the drug with the molten carrier.

In each of the above methods, the extruder should be designed so that it produces a molten feed with the drug crystals distributed in the carrier. Generally, the temperature of the extrudate should be about 10° C. or more above the temperature at which the drug/carrier mixture becomes fluid. In cases where the carrier is a single crystalline material, this temperature is typically about 10° C. or more above the melting point of the carrier. The various zones in the extruder should be heated to appropriate temperatures to obtain the desired extrudate temperature as well as the desired degree of mixing or shear, using procedures well known in the art. As noted above for mechanical mixing, a sufficient shear should be used to produce a substantially uniform molten mixture; however, the shear should not be so high that the crystalline form of the drug is changed or that amorphous drug is formed.

As described above for other methods, it is desirable to maintain a high activity of volatile species in the molten mixture to limit loss of the volatile species from the crystalline form of the drug to acceptable levels. This can be accomplished (i) by adding the volatile species to the extruder feed or (ii) by injecting the volatile species directly into the extruder by metering a controlled amount of volatile species into a separate feed delivery port or (iii) by both (i) and (ii). In any case, sufficient volatile species should be added to ensure that the activity of the volatile species is high enough to maintain the desired form of the crystalline drug.

For example, when the drug is a crystalline hydrate form, it is desirable to keep the water activity of any material in contact with the drug in the 30% to 100% relative humidity (RH) range. This can be accomplished by making sure that the concentration of water in the molten mixture is 30% to 100% of the solubility of water in the molten mixture at the maximum process temperature. In some cases, a small excess of water above the 100% water solubility limit may be added to the mixture.

Once the molten mixture has been formed, it is delivered to an atomizer that breaks the molten feed into small droplets. Virtually any method can be used to deliver the molten mixture to the atomizer, including the use of pumps and various types of pneumatic devices such as pressurized vessels or piston pots. When an extruder is used to form the molten mixture, the extruder itself can be used to deliver the molten mixture to the atomizer. Typically, the molten mixture is maintained at an elevated temperature while delivering the mixture to the atomizer to prevent solidification of the mixture and to keep the molten mixture flowing.

Generally, atomization occurs in one of several ways, including (1) by "pressure" or single-fluid nozzles; (2) by two-fluid nozzles; (3) by centrifugal or spinning-disk atomizers; (4) by ultrasonic nozzles; and (5) by mechanical vibrating nozzles. Detailed descriptions of atomization processes can be found in Lefebvre, *Atomization and Sprays* (1989) or in *Perry's Chemical Engineers' Handbook* (7th Ed. 1997).

There are many types and designs of pressure nozzles, which generally deliver the molten mixture at high pressure to an orifice. The molten mixture exits the orifice as a filament or as a thin sheet that breaks up into filaments, which subsequently break up into droplets. The operating pressure drop across the pressure nozzle ranges from 1 barg to 70 barg, depending on the viscosity of the molten feed, the size of the orifice, and the desired size of the multiparticulates.

In two-fluid nozzles, the molten mixture is exposed to a stream of gas, typically air or nitrogen, flowing at high velocity. In internal-mixing configurations, the molten mixture and gas mix inside the nozzle before discharging through the nozzle orifice. In external-mixing configurations, high velocity gas outside the nozzle contacts the molten mixture. The pressure drop of gas across such two-fluid nozzles typically ranges from 0.5 barg to 10 barg. The activity of volatile species in the gas used in such two-fluid nozzles may be kept high to keep the loss of the desired crystalline form of the drug to acceptable levels.

In centrifugal atomizers, also known as rotary atomizers or spinning-disk atomizers, the molten mixture is fed onto a rotating surface, where it is caused to spread out by centrifugal force. The rotating surface may take several forms, examples of which include a flat disk, a cup, a vaned disk, and a slotted wheel. The surface of the disk may also be heated to aid in formation of the multiparticulates. Several mechanisms of atomization are observed with flat-disk and cup centrifugal atomizers, depending on the flow of molten mixture to the disk, the rotation speed of the disk, the diameter of the disk, the viscosity of the feed, and the surface tension and density of the feed. At low flow rates, the molten mixture spreads out across the surface of the disk and when it reaches the edge of the disk, forms a discrete droplet, which is then flung from the disk. As the flow of molten mixture to the disk increases, the mixture tends to leave the disk as a filament, rather than as a discrete droplet. The filament subsequently breaks up into droplets of fairly uniform size. At even higher flow rates, the molten mixture leaves the disk edge as a thin continuous sheet, which subsequently disintegrates into irregularly sized filaments and droplets. The diameter of the rotating surface generally ranges from 2 cm to 50 cm, and the rotation speeds range from 500 rpm to as high as 100,000 rpm, depending on the desired size of the multiparticulates.

In ultrasonic nozzles, the molten mixture is fed through or over a transducer and horn, which vibrates at ultrasonic frequencies, atomizing the molten mixture into small droplets. In mechanical vibrating nozzles, the molten mixture is fed through a needle vibrating at a controlled frequency, atomizing the molten mixture into small droplets. In both cases, the particle size produced is determined by the liquid flow rate, the frequency of ultrasound or vibration, and the orifice diameter.

In a preferred embodiment, the atomizer is a centrifugal or spinning-disk atomizer, such as the FX1 100-mm rotary atomizer manufactured by Niro A/S (Soeborg, Denmark).

The molten mixture comprising drug and a carrier is delivered to the atomization process as described above. Preferably, the molten mixture is molten prior to congealing for at least 5 seconds, more preferably at least 10 seconds, and most preferably at least 15 seconds so as to ensure the crystalline drug is substantially uniformly distributed in the carrier. It is also preferred that the molten mixture remain molten for no more than about 20 minutes, more preferably no more than 15 minutes, and most preferably no more than 10 minutes to limit the time the drug is exposed to the molten mixture.

When an extruder is used to produce the molten mixture, the times above refer to the mean time from when material is introduced to the extruder to when the molten mixture is congealed. Such mean times can be determined by procedures well known in the art. In one exemplary method, a small amount of dye or other similar compound is added to the feed while the extruder is operating under nominal conditions. Congealed multiparticulates are then collected over time and analyzed for the dye, from which the mean time is determined.

In one embodiment, during the atomization process the droplets of molten mixture are in contact with a second atmosphere. The second atmosphere can be air, nitrogen, helium, argon, carbon dioxide, and the like. In such cases, an additional amount of the volatile species may be added to this second atmosphere to result in a sufficiently high activity of volatile species in the atmosphere that the volatile species in the drug crystals are not removed by vaporization into the second atmosphere.

Once the molten mixture has been atomized, the droplets are congealed, typically by contact with a congealing medium, such as a gas or liquid at a temperature below the solidification temperature of the droplets. Typically, it is desirable that the droplets are congealed in less than about 60 seconds, preferably in less than about 10 seconds, more preferably in less than about 1 second. The congealing step often occurs in an enclosed space to simplify collection of the multiparticulates. A cooling gas or liquid is often introduced into the enclosed space to maintain a constant congealing temperature.

To maintain the crystalline form of the drug and prevent loss of the volatile species and conversion to other crystalline forms, the activity of the volatile species in the congealing medium should be kept high to avoid loss of the volatile species, as previously noted. For example, where the crystalline form is a hydrate, the humidity of the congealing medium should be maintained at 30% RH or higher to maintain the hydrate crystalline form of the drug.

In a separate embodiment, the multiparticulates are formed using a melt-congeal process comprising the steps: (a) providing a drug capable of existing in a crystalline form that includes a volatile species having a vapor pressure of at least 0.01 atmospheres at an operating temperature T; (b) forming a molten mixture comprising the drug and a carrier at the same temperature T; (c) forming droplets from the molten mixture; (d) solidifying the droplets in a congealing medium to form multiparticulates comprising the drug and the carrier; and (e) adding an amount of the volatile species in at least one of steps (b), (c) and (d). The drug may be initially present as (1) a crystalline drug form, (2) a mixture of crystalline drug forms, (3) amorphous drug, or (4) any combination of (1), (2) or (3). The amount of volatile species added in step (e) is sufficient to provide a relative degree of improvement in drug crystallinity of at least 1.1 in comparison to a multiparticulate made using a control method. The control method is essentially the same as above, but without the addition of volatile species. The drug used to form the molten mixture does not need to be in the desired crystalline form, but can be in any form, including other crystalline forms, amorphous drug, or mixtures of crystalline and amorphous drug. In a preferred embodiment, at least a portion of the drug used to form the molten mixture is present in the desired crystalline form. During the process of forming the multiparticulates, the addition of volatile species increases the amount of drug present in the multiparticulate in the desired crystalline form relative to a process wherein none of the volatile species is added.

Additional details of the melt-congeal process are more fully disclosed in commonly assigned U.S. Patent Application Ser. Nos. 60/527,244 ("Improved Azithromycin Multiparticulate Dosage Forms by Melt-Congeal Processes," and 60/527,315 ("Extrusion Process for Forming Chemically Stable Drug Multiparticulates," filed concurrently herewith.

Carriers

The multiparticulates include a pharmaceutically acceptable carrier. By "pharmaceutically acceptable" is meant the carrier must be compatible with the other ingredients of the composition, and not be deleterious to the patient. The carrier functions as a matrix for the multiparticulate and to affect the rate of release of drug from the multiparticulate. The carrier may be a single material or a mixture of two or more materials.

The carrier will generally make up from about 10 wt % to about 95 wt % of the multiparticulate, preferably from about 20 wt % to about 90 wt % of the multiparticulate, and more preferably from about 40 wt % to about 70 wt % of the multiparticulates, based on the total mass of the multiparticulate. The carrier is preferably solid at temperatures of about 40° C. The inventors have found that if the carrier is not a solid at 40° C., there can be changes in the physical characteristics of the composition over time, especially when stored at elevated temperatures, such as at 40° C. Preferably, the carrier is a solid at temperatures of about 50° C., and more preferably at about 60°. It is also desirable that the temperature at which the carrier melts or becomes fluid not be too high. Preferably, the melting point of the carrier not exceed about 200° C. or the melting point of the drug, whichever is less. At excessively high processing temperatures during the multiparticulate formation process, the solubility of the drug in the carrier can be high, resulting in a large percentage of dissolved drug in the molten mixture, which often results in the formation of amorphous drug in the resulting multiparticulate. Accordingly, it is preferred that the carrier have a melting point not exceeding about 180° C., more preferably not exceeding about 150° C., and most preferably not exceeding about 130° C.

Examples of carriers suitable for use in the multiparticulates of the present invention include waxes, such as synthetic wax, microcrystalline wax, paraffin wax, carnauba wax, and beeswax; glycerides, such as glyceryl monooleate, glyceryl monostearate, glyceryl palmitostearate, polyethoxylated castor oil derivatives, hydrogenated vegetable oils, glyceryl mono-, di- or tribehenates, glyceryl tristearate, glyceryl tripalmitate; long-chain alcohols, such as stearyl alcohol, cetyl alcohol, and polyethylene glycol; and mixtures thereof.

Optional Excipients

The multiparticulates may optionally include excipients to aid in forming the multiparticulates, to affect the release rate of azithromycin from the multiparticulates, or for other purposes known in the art.

The multiparticulates may optionally include a dissolution enhancer. Dissolution enhancers increase the rate of dissolution of the drug from the carrier. In general, dissolution enhancers are amphiphilic compounds and are generally more hydrophilic than the carrier. Dissolution enhancers will generally make up about 0.1 to about 30 wt % of the total mass of the multiparticulate. Exemplary dissolution enhancers include alcohols such as stearyl alcohol, cetyl alcohol, and polyethylene glycol; surfactants, such as poloxamers (such as poloxamer 188, poloxamer 237, poloxamer 338, and poloxamer 407), docusate salts, polyoxyethylene alkyl ethers, polyoxyethylene castor oil derivatives, polysorbates, polyoxyethylene alkyl esters, sodium lauryl sulfate, and sorbitan monoesters; sugars such as glucose, sucrose, xylitol, sorbitol, and maltitol; salts such as sodium chloride, potassium chloride, lithium chloride, calcium chloride, magnesium chloride, sodium sulfate, potassium sulfate, sodium carbonate, magnesium sulfate, and potassium phosphate; amino acids such as alanine and glycine; and mixtures thereof. Preferably, the dissolution enhancer is a surfactant, and most preferably, the dissolution enhancer is a poloxamer.

Another useful class of excipients that may optionally be included in the multiparticulates include materials used to adjust the viscosity of the molten mixture used to form the multiparticulates. The viscosity of the molten mixture is a key variable in obtaining multiparticulates with a narrow particle size distribution. Viscosity-adjusting excipients will generally make up 0 to 25 wt % of the multiparticulate, based on the total mass of the multiparticulate. Generally, when a spinning-disk melt-congeal process is employed, it is preferred that the viscosity of the molten mixture be at least about 1 cp and less than about 10,000 cp, more preferably at least 50 cp and less than about 1000 cp. If the molten mixture has a viscosity outside these preferred ranges, a viscosity-adjusting excipient can be added to obtain a molten mixture within the preferred viscosity range. Examples of viscosity-reducing excipients include stearyl alcohol, cetyl alcohol, low molecular weight polyethylene glycol (less than about 1000 daltons), isopropyl alcohol, and water. Examples of viscosity-increasing excipients include microcrystalline wax, paraffin wax, synthetic wax, high molecular weight polyethylene glycols (greater than about 5000 daltons), colloidal silicon dioxide, magnesium silicate, sugars, and salts.

Other excipients may be added to adjust the release characteristics of the multiparticulates or to improve processing and will typically make up 0 to 50 wt % of the multiparticulate, based on the total mass of the multiparticulate. For example, acids or bases may be used to slow or speed the release of the drug, depending on the nature of the drug and other excipients. Examples of bases that can be included in the composition include di- and tri-basic sodium phosphate, di- and tri-basic calcium phosphate, mono-, di-, and tri-ethanolamine, sodium bicarbonate, sodium citrate dihydrate, amine-functionalized methacrylate polymers and copolymers, such as EUDRAGIT E100 from Rohm GmbH, as well as other oxide, hydroxide, phosphate, carbonate, bicarbonate and citrate salts, including various hydrated and anhydrous forms known in the art.

Still other excipients may be added to reduce the static charge on the multiparticulates; examples of such anti-static agents include talc and colloidal silicon dioxide.

Flavorants, colorants, and other excipients may also be added in their usual amounts for their usual purposes.

In one embodiment, the carrier and one or more optional excipients form a solid solution, meaning that the carrier and one or more optional excipients form a single thermodynamically stable phase. In such cases, excipients that are not solid at a temperature of less than about 40° C. can be used, provided the carrier/excipient mixture is solid at a temperature of up to about 40° C. This will depend on the melting point of the excipients used and the relative amount of carrier included in the composition. Generally, the greater the melting point of one excipient, the greater the amount of a low-melting-point excipient that can be added to the composition while still maintaining a carrier in a solid phase at 40° C.

In another embodiment, the carrier and one or more optional excipients do not form a solid solution, meaning that the carrier and one or more optional excipients form two or more thermodynamically stable phases. In such cases, the carrier/excipient mixture may be entirely molten at processing temperatures used to form multiparticulates or one material may be solid while the other(s) are molten, resulting in a suspension of one material in the molten mixture.

When the carrier and one or more optional excipients do not form a solid solution but one is desired, for example, to obtain a specific controlled-release profile, a third excipient may be included in the composition to produce a solid solution comprising the carrier, the one or more optional excipients, and the third excipient. For example, it may be desirable to use a carrier comprising microcrystalline wax and a poloxamer to obtain a multiparticulate with the desired release profile. In such cases a solid solution is not formed, in part due to the hydrophobic nature of the microcrystalline wax and the hydrophilic nature of the poloxamer. By including a small amount of a third component, such as stearyl alcohol, in the formulation, a solid solution can be obtained resulting in a multiparticulate with the desired release profile.

It is preferred that the drug have a low solubility in the molten carrier where solubility is defined as the mass of drug dissolved in the carrier divided by the total mass of carrier and dissolved drug at the processing conditions at which the molten mixture is formed. Low solubility will minimize the formation of amorphous drug during the multiparticulate formation process. Preferably, the solubility of drug in the carrier is less than about 20 wt %, more preferably less than about 10 wt % and even more preferably less than about 5 wt %. The solubility of drug in a molten carrier may be measured by slowly adding crystalline drug to a molten sample of the carrier and determining the point at which drug will no longer dissolve in the molten sample, either visually or through quantitative analytical techniques, such as light-scattering. Alternatively, an excess of crystalline drug may be added to a sample of the molten carrier to form a suspension. This suspension may then be filtered or centrifuged to remove any undissolved crystalline drug and the amount of drug dissolved in the liquid phase can be measured using standard quantitative techniques, such as by high performance liquid chromatography (HPLC). When performing these tests, the activity of volatile species in the carrier, atmosphere, or gas to which the drug is exposed should be kept sufficiently high so that the crystal form of the drug does not change during the test, as previously mentioned.

In one aspect, the multiparticulates are in the form of a "non-disintegrating matrix," meaning that at least a portion of the carrier does not dissolve or disintegrate after introduction of the multiparticulate to an aqueous use environment. In such cases, the drug and optionally one or more of the carriers, for example, a dissolution enhancer, are released from the multiparticulate by dissolution. At least a portion of the carrier does not dissolve or disintegrate and is excreted when the use environment is in vivo, or remains suspended in a test solution when the use environment is in vitro. In this aspect, it is preferred that the carrier have a low solubility in the aqueous use environment. Preferably, the solubility of the carrier in the aqueous use environment is less than about 1 mg/mL, more preferably less than about 0.1 mg/mL, and most preferably less than about 0.01 mg/mL. Examples of suitable low solubility carriers include waxes, such as synthetic wax, microcrystalline wax, paraffin wax, carnauba wax, and beeswax; glycerides, such as glyceryl monooleate, glyceryl monostearate, glyceryl palmitostearate, glyceryl mono-, di- or tribehenates, glyceryl tristearate, glyceryl tripalmitate; and mixtures thereof.

In one embodiment, the multiparticulate comprises about 20 to about 75 wt % drug, about 25 to about 80 wt % of a carrier, and about 0.1 to about 30 wt % of a dissolution-enhancer based on the total mass of the multiparticulate.

In a preferred embodiment, the multiparticulate comprises about 35 wt % to about 55 wt % drug; about 40 wt % to about 65 wt % of an excipient selected from waxes, such as synthetic wax, microcrystalline wax, paraffin wax, carnauba wax, and beeswax; glycerides, such as glyceryl monooleate, glyceryl monostearate, glyceryl palmitostearate, polyethoxylated castor oil derivatives, hydrogenated vegetable oils, glyceryl mono-, di- or tribehenates, glyceryl tristearate, glyceryl tripalmitate; and mixtures thereof; and about 0.1 wt % to about 15 wt % of a dissolution-enhancer selected from surfactants, such as poloxamers, polyoxyethylene alkyl ethers, polysorbates, polyoxyethylene alkyl esters, sodium lauryl sulfate, and sorbitan monoesters; alcohols, such as stearyl alcohol, cetyl alcohol, and polyethylene glycol; sugars such as glucose, sucrose, xylitol, sorbitol, and maltitol; salts such as sodium chloride, potassium chloride, lithium chloride, calcium chloride, magnesium chloride, sodium sulfate, potassium sulfate, sodium carbonate, magnesium sulfate, and potassium phosphate; amino acids such as alanine and glycine; and mixtures thereof.

In another embodiment, the multiparticulates made by the process of the present invention comprise (a) crystalline drug; (b) a glyceride carrier having at least one alkylate substituent of at least 16 carbon atoms; and (c) a polyoxyethylene-polyoxypropylene block copolymer (poloxamer). At least 70 wt % of the drug in the multiparticulate is crystalline. The choice of these particular carrier excipients allows for precise control of the release rate of the drug over a wide range of release rates. Small changes in the relative amounts of the glyceride carrier and the poloxamer result in large changes in the release rate of the drug. This allows the release rate of the drug from the multiparticulate to be precisely controlled by selecting the proper ratio of drug, glyceride carrier and poloxamer. These matrix materials have the further advantage of releasing nearly all of the drug from the multiparticulate. Such multiparticulates are disclosed more fully in commonly assigned U.S. Patent Application Ser. No. 60/527,329 ("Multiparticulate Crystalline Drug Compositions Having Controlled Release Profiles," filed concurrently herewith.

Dosage Forms

Multiparticulates are amenable to use in scaling dosage forms according to the weight of an individual animal in need of treatment by simply scaling the mass of particles in the dosage form to comport with the animal's weight. The multiparticulates may be administered using any known dosage form, including: powders or granules that may be taken orally either dry or reconstituted by addition of water or other liquids to form a paste, slurry, suspension or solution; tablets; capsules; a unit dose packet, sometimes referred to in the art as a "sachet" or an "oral powder for constitution" (OPC); and pills. Various additives may be mixed, ground, or granulated with the compositions of this invention to form a material suitable for the above dosage forms.

The multiparticulates made by the inventive process are designed for controlled release of drug after introduction into a use environment. As used herein, a "use environment" can be either the in vivo environment of the GI tract, subdermal, intranasal, buccal, intrathecal, ocular, intraaural, subcutaneous, vaginal tract, arterial and venous blood vessels, pulmonary tract or intramuscular tissue of an animal, such as a mammal and particularly a human; or the in vitro environment of a test solution, such as a simulated gastric buffer (GB), phosphate buffered saline (PBS) solution, or a model fasted duodenal (MFD) solution.

The multiparticulates may also be post-treated to improve drug crystallinity and/or the stability of the multiparticulate. In one embodiment, the multiparticulates comprise drug and at least one carrier, the carrier having a melting point of $T_m°$ C.; the multiparticulates are treated by at least one of (i) heating the multiparticulates to a temperature of at least about 35° C. and less than about ($T_m°$ C.-10° C.), and (ii) exposing the multiparticulates to a mobility-enhancing agent. This post-treatment step results in an increase in drug crystallinity in the multiparticulates, and typically in improvement in at least one of the chemical stability, physical stability, and dissolution stability of the multiparticulates. Post-treatment processes are disclosed more fully in commonly assigned U.S. Patent Application Ser. No. 60/527,245, ("Multiparticulate Compositions with Improved Stability," filed concurrently herewith.

The invention also provides a method of treating a patient in need of therapy by administering to the patient a therapeutically effective amount of a pharmaceutical composition comprising drug-containing multiparticulates formed by the inventive process. The term "patient" is meant to include all types of animals, including mammals and humans. The amount of drug which is administered will necessarily be varied according to principles well known in the art, taking into account factors such as the severity of the disease or condition being treated and the size and age of the patient. In general, the drug is to be administered so that an effective dose is received, with the effective dose being determined from safe and efficacious ranges of administration known for the drug.

Other features and embodiments of the invention will become apparent from the following examples, which are given for illustration of the invention, rather than for limiting its intended scope.

Example 1

The amount of water required to maintain the dihydrate form of azithromycin while forming multiparticulates by a melt-congeal process was determined as follows. The composition of the multiparticulates was 50 wt % azithromycin dihydrate, 46 wt % of the matrix excipient COMPRITOL 888 ATO (a mixture of 13 to 21 wt % glyceryl mono-behenate, 40 to 60 wt % glyceryl di-behenate, and about 35 wt % glyceryl tri-behenate from Gattefossé Corporation of Paramus, N.J.), and 4 wt % of the poloxamer dissolution enhancer PLURONIC F127 (polyoxyethylene-polyoxypropylene block copolymer, from BASF Corporation of Mt. Olive, N.J.). Mixtures of these materials containing varying amounts of water were prepared and analyzed by PXRD.

To form each mixture, 100 g azithromycin dihydrate, 92 g of the COMPRITOL 888 ATO, and 8 g of the PLURONIC F127 were added to a water-jacketed stainless steel sealed vessel. Various amounts of water were added to each mixture to obtain varying water concentrations. Once sealed, water heated to 90° C. was circulated through the water jacket, and the vessel and sampling line were enclosed in an oven maintained at 90° C. The contents of each vessel were stirred while maintaining the temperature at 90° C., resulting in a suspension of azithromycin dihydrate in the molten carrier. After stirring each vessel for 90 minutes, a sample of the vessel's contents was collected in a glass vial. The vial was capped and removed from the oven, then placed in a bath of liquid nitrogen for approximately 5 minutes to solidify the sample. The sample was equilibrated to room temperature and ground to a powder. A sample of the powder was analyzed by PXRD and the concentration of azithromycin crystalline dihydrate determined by comparison with control samples. The water content of the powder was determined by Karl Fischer titration. Results of these tests are shown in Table 1 and reveal that at least about 2.2 wt % water is needed in the mixtures to maintain high levels of azithromycin dihydrate crystallinity in the melt.

TABLE 1

| Water in Melt Sample (wt %) | Azithromycin Dihydrate Crystallinity (wt %) |
|---|---|
| 3.08 | 95 |
| 2.22 | 93 |
| 1.88 | 91 |
| 0.45 | 68 |
| 0.35 | 57 |

Example 2

Multiparticulates were made comprising 50 wt % azithromycin dihydrate, 47 wt % COMPRITOL 888 ATO, and 3 wt % PLURONIC F127 as follows. First, 492 g azithromycin dihydrate, 462 g of the COMPRITOL 888 ATO, and 30 g of the PLURONIC F127 were blended in a twin shell blender for 20 minutes. This blend was then de-lumped using a Fitzpatrick L1A mill at 3000 rpm, knives forward using a 0.065-inch screen. The mixture was blended again in a twin shell blender for 20 minutes, forming a preblend feed.

The preblend feed was delivered to a B&P 19-mm twin-screw extruder (MP19-TC with a 25 UD ratio purchased from B & P Process Equipment and Systems, LLC, Saginaw, Mich.) at a rate of 124 g/min. Liquid water was pumped into the extruder at a rate of 3.7 g/min. The concentration of water fed to the extruder corresponded to about 3 wt % of the preblend feed. As demonstrated in Example 1, this was a sufficient amount of water to maintain the crystalline dihydrate form of azithromycin at 90° C. The extruder produced a molten feed suspension of azithromycin dihydrate in the COMPRITOL 888 ATO/PLURONIC F127 at a temperature of about 90° C. The mean residence time of azithromycin in the twin-screw extruder was about 60 seconds, and the total mean time the azithromycin was exposed to the molten suspension was less than about 3 minutes. The feed suspension was delivered to the center of a spinning-disk atomizer.

The spinning disk atomizer, which was custom made, consists of a bowl-shaped stainless steel disk of 10.1 cm (4 inches) in diameter. The surface of the disk is heated with a thin film heater beneath the disk to about 90° C. That disk is mounted on a motor that drives the disk of up to approximately 10,000 RPM. The entire assembly is enclosed in a plastic bag of approximately 8 feet in diameter to allow congealing and to capture microparticulates formed by the atomizer. Air is introduced from a port underneath the disk to provide cooling of the multiparticulates upon congealing and to inflate the bag to its extended size and shape. The surface of the spinning disk atomizer was maintained at about 90° C. and the disk was rotated at 5500 rpm while forming the azithromycin multiparticulates.

A suitable commercial equivalent to this spinning disk atomizer is the FX1 100-mm rotary atomizer manufactured by Niro A/S (Soeborg, Denmark).

The particles formed by the spinning-disk atomizer were congealed in ambient air and a total of 561 g of multiparticulates were collected. Samples of the multiparticulates were evaluated by PXRD, which showed that 93±6% of the azithromycin in the multiparticulates was in the crystalline dihydrate form.

Control 1

For Control 1 (C1), multiparticulates were produced as described in Example 2 with the variables noted in Table 2, but without adding water to the extruder.

TABLE 2

| Ex. No. | Formulation (Azithromycin/ COMPRITOL 888 ATO/PLURONIC F127, wt/wt/wt) | Preblend Feed Rate (g/min) | Water Feed Rate (g/min) | Disk speed (rpm) | Disk Temp (° C.) | Batch size (g) |
|---|---|---|---|---|---|---|
| 2 | 50/47/3 | 124 | 3.7 | 5500 | 90 | 984 |
| C1 | 50/47/3 | 140 | 0 | 5500 | 90 | 5000 |

Samples of the multiparticulates of C1 were evaluated by PXRD, which showed that 73±7% of the azithromycin in the multiparticulates was in the crystalline dihydrate form.

Taken together, the data from Example 2 and Control 1 show that maintaining a water concentration of only 3 wt % in the molten mixture resulted in a much greater percentage of the more stable crystalline dihydrate form in the multiparticulates, as compared with no water addition. In particular, the addition of water to the molten feed resulted in a relative degree of improvement in crystallinity of (100 wt %–73 wt %)/(100 wt %–93 wt %) or 3.9.

Example 3

Multiparticulates comprising 40 wt % azithromycin dihydrate and 60 wt % microcrystalline wax were prepared using the following melt-congeal procedure. First, 150 g of microcrystalline wax and 5 g of water were added to a sealed, jacketed stainless-steel tank equipped with a mechanical mixing paddle. Heating fluid at 97° C. was circulated through the jacket of the tank. After about 40 minutes, the mixture had melted, having a temperature of about 94° C. Next, 100 g of azithromycin dihydrate that had been preheated at 95° C. and 100% RH and 2 g of water were added to the melt and mixed at a speed of 370 rpm for 75 minutes, resulting in a feed suspension of the azithromycin dihydrate in microcrystalline wax.

Using a gear pump, the feed suspension was then pumped at a rate of 250 cm³/min to the center of the spinning-disk atomizer of Example 2, rotating at 7500 rpm, the surface of which was maintained at 100° C. The particles formed by the spinning-disk atomizer were congealed in ambient air. The mean particle size was determined to be 170 μm using a Horiba LA-910 particle-size analyzer. Samples of the multiparticulates were also evaluated by PXRD, which showed that 93±10% of the azithromycin in the multiparticulates was in the crystalline dihydrate form.

Control 2

Multiparticulates having the same composition as those of Example 3 were prepared as in Example 3, except that the azithromycin dihydrate was preheated to 100° C. at ambient relative humidity and no additional water was added to the feed tank when the azithromycin was mixed with the molten microcrystalline wax. The mean particle size was determined to be 180 μm using a Horiba LA-910 particle-size analyzer.

Samples of the multiparticulates were also evaluated by PXRD, which showed that only 67% of the azithromycin in the multiparticulates was crystalline, and that both dihydrate and non-dihydrate crystalline forms were present in the multiparticulates.

Taken together, the data from Example 3 and Control 2 show that the addition of even small amounts of the volatile species water to the molten feed maintains a high percentage of crystalline dihydrate in the multiparticulates. The addition of water resulted in a relative degree of improvement in crystallinity of (100 wt %–67 wt %)/(100 wt %–93 wt %) or 4.7.

Example 3

Multiparticulates were made comprising 50 wt % azithromycin dihydrate, 47 wt % COMPRITOL 888 ATO, and 3 wt % poloxamer 407 (of a block copolymer of ethylene and propylene oxides commercially available as PLURONIC F127 or LUTROL F127) using the following procedure. First, 140 kg azithromycin dihydrate was weighed and passed through a Quadro Comil 196S with a mill speed of 900 rpm. The mill was equipped with a No. 2C-075-H050/60 screen (special round, 0.075"), a No. 2F-1607-254 impeller, and a 0.225 inch spacer between the impeller and screen. Next, 8.4 kg of the LUTROL F127 and then 131.6 kg of the COMPRITOL 888 ATO were weighed and passed through a Quadro 194S Comil mill. The mill speed was set at 650 rpm. The mill was equipped with a No. 2C-075-R03751 screen (0.075"), a No. 2C-1601-001 impeller, and a 0.225-inch spacer between the impeller and screen. The mixture was blended using a Gallay 38 cubic foot stainless-steel bin blender rotating at 10 rpm for 40 minutes, for a total of 400 rotations, forming a preblend feed.

The preblend feed was delivered to a Leistritz 50 mm twin-screw extruder (Model ZSE 50, American Leistritz Extruder Corporation, Somerville, N.J.) at a rate of about 20 kg/hr. The extruder was operated in co-rotating mode at about 100 rpm, and interfaced with a melt/spray-congeal unit. The extruder had five segmented barrel zones and an overall extruder length of 20 screw diameters (1.0 m). Water was injected into barrel number 2 at a rate of 6.7 g/min (2 wt %). The extruder's rate of extrusion was adjusted so as to produce a molten feed suspension of the azithromycin dihydrate in the COMPRITOL 888 ATO/LUTROL F127 at a temperature of about 90° C.

The feed suspension was delivered to the heated spinning-disk atomizer of Example 2, rotating at 6400 rpm and maintained at a temperature of about 90° C. The maximum total time the azithromycin was exposed to the molten suspension was less than 10 minutes. The particles formed by the spinning-disk atomizer were cooled and congealed in the presence of cooling air circulated through the product collection chamber. The mean particle size was determined to be about 200 μm using a Malvern particle size analyzer.

The so-formed multiparticulates were post-treated by placing a sample in a sealed barrel that was then placed in a controlled atmosphere chamber at 40° C. for 10 days. Samples of the post-treated multiparticulates were evaluated by PXRD, which showed that about 99% of the azithromycin in the multiparticulates was in the crystalline dihydrate form.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A method of forming multiparticulates, comprising a crystalline drug that includes a volatile species having a vapor pressure of at least 0.01 atmosphere at an operating temperature T followed by the following steps:
   (a) forming a molten mixture comprising said crystalline drug, a dissolution enhancer, and a carrier at said temperature T wherein said carrier is a glyceride having at least one alkylate substituent of at least 16 carbon atoms;
   (b) forming droplets from said molten mixture; and
   (c) congealing said droplets in a congealing medium to form multiparticulates comprising said drug and said carrier, wherein at least 95 wt % of said drug remains in its initial crystalline form;
wherein said drug is azithromycin dihydrate; and
wherein said volatile species is water and is added during (a).

2. The method of claim 1 wherein said volatile species is added in an amount sufficient to provide a relative degree of improvement in drug crystallinity of at least 1.1 in comparison to multiparticulates made by a control method comprising the method of claim 1, steps (a) through (c).

3. The method of claim 1 wherein said volatile species is injected into an extruder containing said molten mixture.

4. The method of claim 1 wherein said volatile species is in the form of a vapor.

5. The method of claim 1 wherein said volatile species is in the form of a liquid.

6. The method of claim 1 wherein said dissolution enhancer is a poloxamer.

* * * * *